United States Patent [19]  [11] Patent Number: 5,041,244
Baron  [45] Date of Patent: Aug. 20, 1991

[54] OPHTHALMIC LIQUID SUNGLASSES

[75] Inventor: Neville A. Baron, Secaucus, N.J.

[73] Assignee: Liquid Sunglasses Corporation, Line Lexington, Pa.

[21] Appl. No.: 524,710

[22] Filed: May 16, 1990

Related U.S. Application Data

[63] Continuation of Ser. No. 234,755, Aug. 22, 1988, abandoned, which is a continuation-in-part of Ser. No. 935,843, Nov. 28, 1986, Pat. No. 4,765,977.

[51] Int. Cl.5 .................. F21V 9/04; A01N 35/00; A61K 31/13
[52] U.S. Cl. .................... 252/589; 252/582; 424/59; 424/78; 514/686; 514/687; 604/294
[58] Field of Search ................. 252/589, 582; 424/59, 424/78; 514/721, 686, 687; 604/294

[56] References Cited

U.S. PATENT DOCUMENTS

| | | | |
|---|---|---|---|
| 3,821,363 | 6/1974 | Black | 424/59 |
| 4,230,690 | 10/1980 | Yamauchi et al. | 424/78 |
| 4,271,144 | 6/1981 | Holly | 424/78 |
| 4,323,694 | 4/1982 | Scala | 424/59 X |
| 4,636,212 | 1/1987 | Posin | 623/6 |
| 4,686,099 | 8/1987 | Palinczar | 424/47 |
| 4,788,007 | 11/1988 | Baron | 252/589 |
| 4,923,693 | 5/1990 | Michalos | 424/59 |

*Primary Examiner*—John S. Maples
*Assistant Examiner*—Richard Treanor
*Attorney, Agent, or Firm*—Eric P. Schellin

[57] ABSTRACT

Ophthalmic dosages of chromophores in aqueous gel to block transmission of all or various spectrums of U.V. from the eyes, when used as ophthalmic liquid sunglasses.

5 Claims, No Drawings

OPHTHALMIC LIQUID SUNGLASSES

BACKGROUND OF THE INVENTION

This application is a continuation of application Ser. No. 234,755, filed Aug. 22, 1988, abandoned, which is a continuation-in-part of U.S. application Ser. No. 935,843, filed Nov. 28, 1986, now U.S. Pat. No. 4,765,977, and sets forth: (1) additional chromophores of ethylenically unsaturated derivatives of dihydroxy benzophenones as liquid sunglasses; (2) the percent transmission of particular wavelengths of light using certain amounts of liquid sunglasses; and (3) a method of injecting or tatooing chromophores below the corneal epithelium in order to set-up high absorption or low transmission of harmful light rays.

Although ultraviolet radiation has long been recognized as a factor in the development of cutaneous cancer, aging of the skin, and mutagenic changes, it is only within the last decade or less that ultraviolet radiation has been universally recognized as a causative factor in ocular pathogenesis.

In humans, the eye has evolved into a sophisticated organ having neurophysiologic responses to photons in a certain portion of the electromagnetic spectrum, that provides a constant detailed map of the immediate environment. The action spectrum for these responses lie primarily within the 400–700 nm wavelength range, which has been labeled the visible spectrum or "light".

The maximum of the eye's spectral response corresponds roughly to the maximum of solar spectral irradiance. Because solar UV radiation is present during most of the daylight hours, the eye may be exposed daily to some amount of solar ultraviolet radiation throughout life. Wavelengths shorter than approximately 290 NM or UV-C are partially or completely absorbed within the cornea and conjunctival. The acute effects of exposure to these wavelengths are primarily those of conjunctivitis and a corneal inflammation reaction known as photokeratitis. The inflammatory reaction of the outermost layer of the eye to UV-C and UV-B radiation can be similar to that of the skin in some respects.

The clinical progress or picture of photokaratitis follows a characteristic course. For example, after exposure, there is a period of latency which varies somewhat inversely with the amount of exposure. The latent period may be as short as 30 minutes or as long as 24 hours but it is typically 6 to 12 hours.

Conjunctivitis, which is often accompanied by an erythema of the skin surrounding the eyelids, is associated with the sensation of a foreign body or "sand" in the eyes, varying degrees of photophobia (intolerance to light), lacrimation (tearing), and blepharospasm (spasm of lid muscles). Corneal pain can be very severe, and the individual is usually incapacitated for some period of time. These acute symptoms usually last from 6 to 24 hours, and almost all discomfort disappears within 48 hours. Vary rarely does conjunctivitis causing exposure result in permanent damage.

However, unlike the skin, the ocular system does not develop tolerance to repeated ultraviolet exposure. Swelling or shrinking of groups of corneal epithelail cells leads to visibly recognizable stippling or irregular mosaic granulation of the corneal surface. With UV doses greater than the threshold for photokeratitis, surface epithelial cells show nuclear fragmentation, mid-epithelial cells show vacuole formation, basal bells show inhibition of mitosis and clouding of the corneal stroma occurs. Inflammation is also present in the conjunctival where vasodilation, edema, and inflammtory cell infiltrate is followed by desquamation.

Because wavelengths longer than 290 nm are largely transmitted by the cornea, the underlying lens and iris are exposed to UV-A. The lens absorbs essentially all of the UV-A striking it and is therefore the ocular tissue especially susceptible to alteration by UV-A exposure of the eye. The possible production of lenticular cataracts in humans by UV-A exposure is therefore a cause of major concern.

Any alterations of the lens or its capsule that result in apparent decreased transmission or increased scattering of visible light may be called a cataract. Minimal alterations, although detectable by careful biomicroscopic examination, cause no change in routine visual acuity, but more marked alterations of light transmission may impair or eliminate vision. The term cataract is often reserved for this symptomatic decrease in vision.

SUMMARY OF THE INVENTION

Accordingly, it is a principal object of the present invention to provide an aqueous dispersion containing an ocular chromophore that establishes an ultraviolet absorption spectrum equilibrium between the tear film and the epithelium of the cornea of mammals, in the UV-A and UV-B wavelengths.

It is another object of the present invention to provide an aqueous dispersion containing an ocular chromophore that establishes an ultraviolet absorption spectrum equilibrium between the tear film and the epithelium of the cornea of mammals, which is non-toxic to the corneal epithelium in functional concentrations.

It is a further object of the present invention to provide an aqueous dispersion containing an ocular chromophore together with a high molecular weight polymer vehicle that maintains ultraviolet absorption spectrum equilibrium between the tear film and the epithelium of the cornea of mammals for about 2 to 4 hours.

In general, the invention objective is accomplished by preparing an aqueous dispersion containing from about 1 to about 10% by weight of a fat or lipid soluble chromophore of 2-ethylhexyl-p-methoxycinnamate, the same percentages of a mixture of 2-ethylhexyl-p-methoxycinnamate and octyl methoxycinnamate together with a high molecular weight polymer, or ethylenically unsaturated derivatives of dihydroxy benzophenones selected from the group consisting of

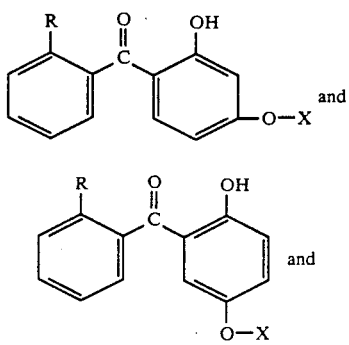

-continued

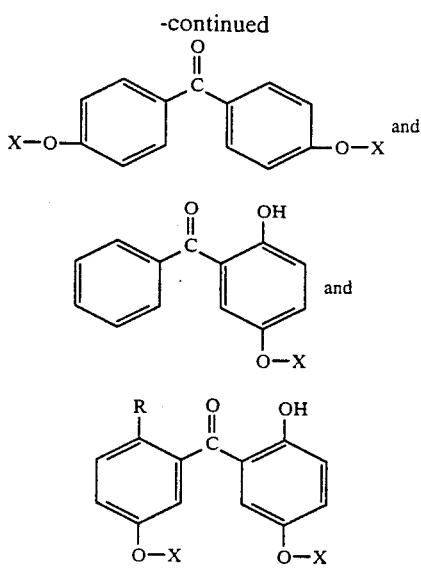

where X is an ethylenically unsaturated radical selected from the group consisting of acryloxybetahydroxypropyl and wherein R is a radical selected from the group consisting of hydrogen and hydroxyl, and topically applying drops of said dispersion in the eye of a mammalian subject.

These and other objects of the invention will become more apparent from the following detailed description.

DETAILED DESCRIPTION OF THE INVENTION

While the visible spectrum of light is around 400 nm and above, Ultra Violet-A or UV-A is from around 400 nm down to about 325 nm. Ultra Violet-B or UV-B ranges from around 325 nm down to about 290 nm.

Absorption of radiation by the cornea and lens of the human eye is such that very little radiation of wavelengths shorter than 390 nm, which is in the UV-A range, reaches the retina. In persons with no lens, much of the UV-A striking the eye reaches the retina. UV-A irradiation of normal phakic animals with and without the presence of UV-A sensitizing compounds produces damage to the retina.

Multiple animal models have been used to study biochemical alteration in the retina by UV-A. For example, free-radical scavenger studies apparently indicate that UV-A damages turkey retina via lipid peroxidation, and protein and RNA synthesis in dogfish retinal rods were suppressed by irradiation at 340-380 nm. However, in protein extracts, the rat retina protein synthesis was suppressed by 320 nm radiation and not by 340 or by 360 nm exposure.

UV-A induced morphological and histological changes in the retina were studied by exposing the intact whole eye of mice. In this study, thinning of the photoreceptor outer segments of mouse retina was noted 10 weeks after exposure to 365 nm radiation. The animals were exposed for 12 hours each day to UV-A fluorescent lamps (450 uW/cm$^2$). At 16 weeks, the outer rod segments were further destroyed and remnants were partially digested by phagocytic cells.

Laser radiation in the region of 350-365 nm also causes damage to outer segments of rhesus monkey retina and chronic exposure of rats to high intensity UV-A over 3 years led to atrophy of the first neuron, partial degeneration of the second neuron, and destruction of retinal structure.

Therefore, there is reason to believe that UV-A photochemically induces retinal lesions if the ocular spectral transmission of the species in question allows UV-A to reach the retina.

Further, experimental exposures of animals and humans indicate that for wavelengths shorter than approximately 310 nm, which is in the UV-B or 325-290 nm wavelength, keratitis and alteration of the cornea are major ocular hazards. These reactions and effects are usually painful but reversible. This UV-induced alteration of the cornea appears to follow a photochemical mechanism.

Ultraviolet wavelengths longer than 290 nm may reach the lens, the iris, and the aqueous humor (anterior chamber). Experimental evidence in rabbits and monkeys indicates that permanent lenticular cataracts may be produced by single, high-irradiance or long-exposure durations to UV-B or UV-A ranges. Furthermore, in albino mice, cataracts may be produced by multiple daily UV-A exposures that are below the single-exposure threshold dose of observable corneal damage.

Biochemical studies on human and other mammal lenses indicate that UV-A appears to induce lenticular cataracts via alteration of lens crystalline proteins from soluble, lower-molecular-weight crystallines to insoluble, higher-molecular-weight crystallines, which may cause light scattering within the lens (cataract), and there is evidence that long-term daily UV-A exposure destroys the retinas of mice.

G. Klecak[1] has conducted studies on the use of 2-ethyl-hexyl-p-methoxycinnamate alone or together with octyl methoxycinnamate to determine the light screening activities of these compounds in the UV-A and UV-B ranges.

[1]: "Determination Of The Lightscreening Activity In The UV-A Range Of 8 Preparations In The Animal Model". GIVAUDAN SA, April 1985.
"Determination Of The Lightscreening Activity In The UV-A Range Of 6 Preparations In The Animal Model". GIVAUDAN SA, April 1985.
"Determination Of The Lightscreening Activity In The UV-B Range". GIVAUDAN SA, April 1985.

Determinations of the sun protective activity of these compounds on humans in the UV-A range has also been conducted by G. Klecak et al[2]; however, there has been no determination of the potential of these compounds for use as liquid sunglasses applied topically in the eyes.

[2]: "Determination Of The Light Protective Activity In The UV-A Range Of 2 Sunscreen Preparations On Patients Under PUVA-TREATMENT" GIVAUDAN SA, April 1985.

The present invention is directed to an aqueous dispersion of a chromophore and a high molecular weight polymer which forms a viscous dispersion and is used to establish UV-A and UV-B absorption spectrum equilibrium between the tear film and epithelium of the cornea of mammals when topically applied into the eyes.

Prolongation of the equilibrium appears to be accomplished by either the slow release of the chromophore from the viscous dispersion and/or a slow erosion of the viscous surface. The chromophore containing viscous or gel compositions of the present invention have a prolonged retention time in the eyes and remain in contact with the surface of the eye for periods of from about 2 to about 4 hours.

The present invention is directed to an aqueous dispersion of a chromophore and a high molecular weight polymer which forms viscous dispersions and can be used to prolong the curation of the chromophore when the gel is applied into the eye. The prolongation of chromophore activity is accomplished through a slow release from the gel matrix and/or a slow erosion of gel surface. Also, the chromophore containing gel compositions of the present invention have a prolonged retention time in the eye and remain in contact with the surface of the eye for an extended period of time.

The polymers used in the present invention have a molecular weight of from about 1 million to about 6 million, and are characterized by carboxylic or anhydride functional groups and preferably contains from 2 to 7 carbon atoms per functional group. The gels which form during the preparation of the chromophore/polymer dispersion have a viscosity of from about 40,000 to about 300,000 cps at 20 rpm (spindle 7) at 25° C. generated by an RVT Brookfield Viscometer, and preferably from about 75,000 to about 200,000 cps. Suitable polymers useful in the present invention are carboxypolymethylene, a carboxy vinyl polymer, (available under the trade name Carbopol from the B. F. Goodrich Company); and ethylene maleic anhydride, (available under the trade name EMA from the Monsanto Company). The polymers are used in the gel compositions at a level of from about 2 to about 8 percent by weight.

The chromophore material is represent in the gel composition at a level to effectively form a film in the entire eye, and establish an ultraviolet absorption spectrum equilibrium between the tear film and the epithelium of the cornea against UV-A and UV-B wavelengths. Non-toxic levels of the chromophore compounds which accomplish this effect are from about 1 to about 8% by weight.

The cornea is viewed as a fat-water-fat sandwich. Chemical analysis shows the lipid content of the epithelium and endothelium to be 100 times greater than that of the corneal stroma. As a result, the epithelium and endothelium are relatively impermeable to electrolytes but are readily penetrated by fat-soluble substances.

Several methods are used to prepare chromophore/polymer compositions of the invention. One Method, I, involves dispersing the polymer in water followed by the addition of a basic chromophore to neutralize the polymer. The neutralization is responsible for the formation of a hydrogel complex of the chromophore and polymer. The final pH is dependent upon the basicity of the chromophore and the amount added. If the chromophore is not sufficiently basic, the pH of the hydrogel is adjusted by adding a basic material, such as ammonium hydroxide, sodium hydroxide, ethanolamine or other basic compounds to provide a desired pH. The preferred pH is of from about 4.5 to about 8.5 in the chromophore/polymer gel formulations. Also it should be noted that the chromophore can be added to a hydrogel formed by addition of a basic agent to the polymer to first form the gel, followed by addition of the chromophore in any desired concentration.

In a second Method, II, a salt of the chromophore and the polymer is prepared. The chromophore salt is prepared by dispersing the polymer in an inert organic solvent, such as hexane, benzene or chloroform, to form a slurry. Thereafter, a solution of the chromophore in the solvent is added to the slurry. An acid-base neutralization reaction takes place in which the polymer chromophore product precipitates from the solvent. After removal of the solvent, a finely divided powdered solid remains. The solid mass can be reduced to fine particles by grinding. Thereafter, a gel is prepared by dispersion of the finely divided powdered product in water.

A third Method, III, utilizes the acid salt form of the chromophore. A base, such as sodium hydroxide is used to neutralize an aqueous dispersion of the polymer and form a gel followed by addition of the acid salt form of the chromophore.

Duration of activity of gel formulations containing the chromophores prepared by all three methods is substantial. For example, 2-ethylhexyl-p-methoxycinnamate complexed with carboxypolymethylene by Method I. gives gel formulations that remain in the conjunctival sac of a rabbit for a period of 2 to 4 hours. In a further embodiment of the invention finely divided particles of a chromophore salt of the polymer prepared in accordance with Method II, is suspended in a non-aqueous vehicle, such as stabilized oil, e.g. mineral oil, vegetable oil and silicone fluid. Thereafter, the suspended particles are administered directly into the eye. A gel forms between the tear film and epithelium of the cornea. 2-ethylhexyl-p-methoxycinnamate salts of carboxypolymethylene containing 4 to 6% by weight per dose is active as a U.V. absorber in albino rabbit eyes for 2 to 4 hours.

The examples following will further illustrate various features of the invention but is not intended to limit the invention scope, which is set forth in the appended claims:

EXAMPLE 1

A salt form of carboxypolymethylene and 2-ethylhexyl-p-methoxycinnamate is prepared by Method II. Six grams of carboxypolymethylene (available under the trade name Carbopol 940 from B. F. Goodrich Co.) is stirred into 30 ml of hexane. Four grams of 2-ethylhexyl-p-methoxycinnamate is dissolved in 30 ml of hexane. The 2-ethylhexyl-p-methoxycinnamate solution is then blended with the suspension of carboxypolymethylene. An acid-base neutralization reaction occurs to form a salt of 2-ethylhexyl-p-methoxycinnamate and the polymer. The salt form of the polymer and 2-ethylhexyl-p-methoxycinnamate is recovered from the hexane carrier in the form of a finely divided powder containing about 35 to 40 percent by weight of 2-ethylhexyl-p-methoxycinnamate.

Two gel formulations are prepared containing the 2-ethylhexyl-p-methoxycinnamate/carboxypolymethylene salt. The gel formulations contain the ingredients indicated hereinbelow in Table I at the indicated level.

TABLE I

| Ingredient | % by weight | |
| --- | --- | --- |
| | Formulation A | Formulation B |
| Carboxypolymethylene/ 2-ethylhexyl-p-methoxycinnamate salt | 6.0 | 6.0 |
| Benzalkonium Chloride (U.S.P.) | 0.01 | 0.01 |
| Sodium Hydroxide (3N) approx. | pH 5.35 approx. | approx. 5.35 |
| Purified Water | 94 | 94 |

Obtaining 100 grams of finished gel consists of adding Benzalkonium Chloride to 80 grams of purified water. The benzalkonium chloride solution is stirred as the salt form powder of carboxypolymethylene/2-ethylhexyl-p-methoxycinnamate is added. The solution is stirred to wet as much of the salt form powder as possible before formation of the gel in about one to two minutes. Stirring is continued until there is no further apparent hydration. Sodium hydroxide is then added incrementally to provide the indicated pH. Purified water is stirred into the gel to bring the gel weight to 100 gram. The gel preparation is autoclaved at 120° C. for 20 minutes followed by fast exhaust. Any containing air bubbles in the furnished gel can be removed by centrifugation.

Using the Ferranti-Shirley Viscometer under the following conditions: 3× Switch Position, 60 seconds sweep, medium cone and 100 rpm spring constant, the following approximate viscosities are obtained:

TABLE II

|  | A 25° C. | A 37° C. | B 25° C. | B 37° C. |
|---|---|---|---|---|
| Plastic Viscosity (CPS) | 740 | 708 | 546 | 804 |

Topically applied chromophore gel compositions of the invention, when placed in the eyes via drops, provide a film of U.V. absorption spectrum equilibrium between the tear film and the epithelium of the cornea, and in addition to absorbing ultraviolet light which regular sun-glass would absorb, the gel absorbs the estimated 30 to 35% of UV-A and UV-B radiation that normally reaches the eye from points above, below and from the sides of regular sun-glasses.

Moreover, the gel compositions of the invention contain about 92 percent by weight of water in the polymer matrix and are clear. Therefore, the vision of the subject treated with the gel does not become blurred because the refractive index of the gel is similar to that of tears.

EXAMPLE 2

In accordance with method III, the acid salt form of 50/50 mixture of 2-ethylhexyl-p-methoxycinnamate/octyl methoxycinnamate is incorporated within a gel made from ethylene maleic anhydride (available under the trade name of EMA-91 from Monsanto. Two gel preparations are prepared and contain the ingredients indicated herein below in Table III.

TABLE III

| Ingredient | % by weight Formulation A | Formulation B |
|---|---|---|
| Ethylene maleic anhydride | 3.38 | 5.0 |
| 2-ethylhexyl-p-methoxy-cinnamate hydrochloride/ octyl methoxycinnamate hydrochloride | 4.0 | 4.0 |
| 28% ammonium hydroxide | 2.27 | 3.5 |
| Mannitol, N.F. | 1.0 | 2.0 |
| Benzalkonium chloride (U.S.P.) | 0.01 | 0.01 |
| Purified water (Balance to 100%) | Balance | |

Preparing 100 grams of finished gel consists of adding ethylene maleic anhydride to the vortex of 25 ml of vigorously stirred water using a high speed mixer. One minute of mixing is sufficient to wet and disperse the polymer. Ammonium hydroxide was added to the dispersion and mixed for one or two minutes until a rigid gel was formed. 2-ethylhexyl-p-methoxycinnamate,hydrochloride/octyl methoxycinnamate hydrochloride, mannitol and benzalkronium chloride were dissolved in 15 ml of purified water and added to the gel. This mixture is stirred for 4 minutes and a pH reading of approximately 5.1 is obtained.

Using a Brookfield RVT Viscometer at 20 rpm equipped with spindle #7, and also using a Ferranti-Shirley Viscometer under the following conditions; 3× switch position, 60 second sweep, medium cone and 100 rpm constant, the following viscosity determinations are obtained:

TABLE IV

|  | 24° C. | 25° C. | 37° C. |
|---|---|---|---|
| A |  |  |  |
| Brookfield Viscosity (cps) | 123,000 | — | — |
| Ferranti-Shirley Plastic Viscosity (cps) | — | 434 | 384 |
| B |  |  |  |
| Brookfield Viscosity (cps) | 109,000 | — | — |
| Ferranti-Shirley Plastic Viscosity (cps) | — | 692 | 558 |

Among the means suitable for placing the chromophores of the invention into the eyes is a "tatooing" or injection technique to administer the chromophore below the corneal epithelium and into the stroma to a point short of the Descemet's membrane and the endothelium, in order to provide via implant a permanent to semi-permanent U.V. barrier, which would eventually be dissapated by normal tissue metabolism or physical dissapation. The injection or tatooing is accomplished using a hydraulically operated hypodermic jet injection apparatus to inject the chromophore to a depth of about 2 to 3 microns. The apparatus rapidly injects metered quantities of chromophore at high pressure and velocity through a jet tip. The chromophore agent makes its own opening into the stroma and penetrates to a suitable depth for implantation. Dosage adjustments of from 0.1 to 1.0 cc is accomplished by turning an adjustment knob located at the rear of the apparatus. Each 360° turn of the adjustment knob is equal to 0.1 cc.

Many changes can be made in the use of the gel-chromophore of the invention, and it is contemplated that the chromophore per se can be placed in an intraocular lens before placement of the lens in the eye to effect a screen for UV-A and UV-B radiations.

What is claimed is:

1. A method for delivering a physiological acceptable ophthalmic chromophore dosage to the eye to establish a U.V. absorption spectrum equilibrium between the tear film and epithelium of the cornea of the eye in the UV-A and UV-B wavelengths, comprising: treating the eye with a composition including as an active ingredient a compound selected from the group consisting of

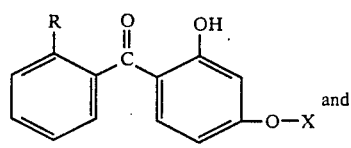 and

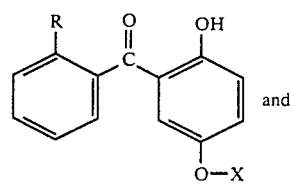 and

-continued

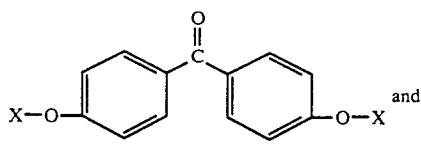

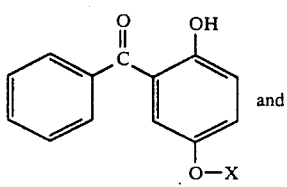

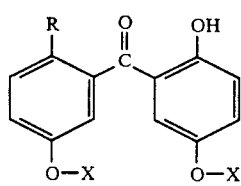

where X is an ethylenically unsaturated radical and R is either hydrogen or an hydroxyl group; in an aqueous gel forming carrier consisting of a high molecular weight ethylene-maleic anhydride polymer having a molecular weight in excess of 1,000,000, said active compound being in an amount of between about 1 to 8 percent by weight and said high molecular weight ethylene-maleic anhydride is in an amount of between about 2 to 8 percent by weight and the balance being water.

2. A method for establishing a U.V. absorption spectrum equilibrium between the tear film and epithelium of the cornea of the eye in the UV-A and UV-B wavelengths, comprising treating the cornea with a composition including as an active ingredient a compound selected from the group consisting of:

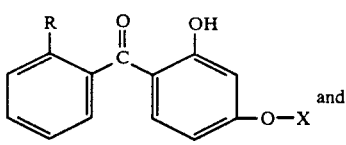

-continued

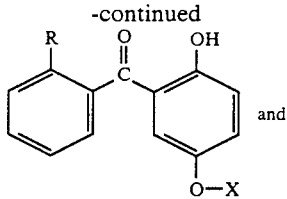

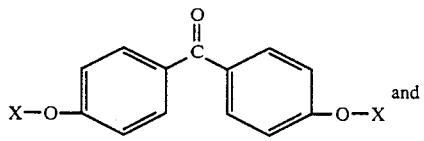

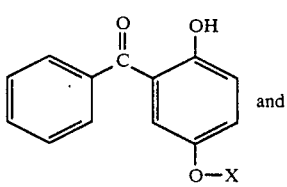

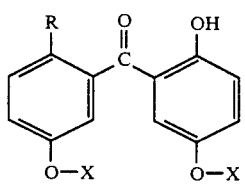

where X is acryloxybetahydroxypropyl and wherein R is selected from the group consisting of hydrogen and hydroxyl in a physiologically acceptable aqueous gel forming carrier.

3. The method of claim 2, wherein the carrier comprises a high molecular weight ethylene-maleic anhydride polymer having a molecular weight in excess of 1,000,000 and in amount of between about 2 to 8 percent by weight; and said active ingredient is in an amount of between about 1 to 8 percent by weight and the balance is water.

4. A method for establishing a U.V. absorption spectrum equilibrium between the tear film and epithelium of the cornea of the eye in the UV-A and UV-B wavelengths, comprising treating the cornea with a composition including as an active compound a compound selected from the group consisting of 2-hydroxy-4-(2-hydroxy-3-methacrylyloxy) propoxylbenzophenone, 4-t-butyl-4-methoxy-dibenzoylmethane and mixtures thereof in a physiological acceptable aqueous gel forming carrier.

5. The method of claim 4 wherein the carrier comprises a high molecular weight ethylene-maleic anhydride polymer having a molecular weight in excess of 1,000,000 and in amount of between about 2 to 8 percent by weight; and said active ingredient is in an amount of between about 1 to 8 percent by weight and the balance is water.

* * * * *